United States Patent [19]
Crabb

[11] Patent Number: 5,820,584
[45] Date of Patent: Oct. 13, 1998

[54] DUODENAL INSERT AND METHOD OF USE

[76] Inventor: Jerry A. Crabb, 4363 White Oak Dr., Buford, Ga. 30518

[21] Appl. No.: 919,381

[22] Filed: Aug. 28, 1997

[51] Int. Cl.⁶ .................................................. A61M 31/00
[52] U.S. Cl. ........................... 604/49; 604/264; 604/270; 604/280
[58] Field of Search .................................... 604/264, 270, 604/275, 280, 43, 49, 51

[56] References Cited

U.S. PATENT DOCUMENTS

| | | |
|---|---|---|
| 4,133,315 | 1/1979 | Berman et al. . |
| 4,315,509 | 2/1982 | Smit . |
| 4,416,267 | 11/1983 | Garren et al. . |
| 4,501,264 | 2/1985 | Rockey . |
| 4,607,618 | 8/1986 | Angelchik . |
| 4,648,383 | 3/1987 | Angelchik . |
| 5,037,387 | 8/1991 | Quinn et al. .............................. 604/51 |
| 5,057,091 | 10/1991 | Andersen ................................. 604/270 |
| 5,152,756 | 10/1992 | Quinn et al. ............................ 604/270 |
| 5,401,241 | 3/1995 | Delany . |
| 5,611,787 | 3/1997 | Demeter et al. ........................ 604/270 |

Primary Examiner—John D. Yasko
Attorney, Agent, or Firm—Hinkle & Associates, P.C.

[57] ABSTRACT

A duodenal insert (20) comprises an elongated open-ended tube (22) having a passageway that extends from a first end (24) to a second end (26) for transporting partially digested food materials from the stomach (6) for a predetermined distance below the stomach to interrupt or reduce the intermixing of digestive fluids with the partially digested food materials. The duodenal insert is anchored within a pylorus (10) by a pair of spaced apart first and second rings (32 and 34) in a seated and sandwiched arrangement with the pylorus. Bores (38) and splits (40) are optionally disposed through the open-ended tube to provide the digestive fluids controlled access to the interior of the duodenal insert.

11 Claims, 2 Drawing Sheets

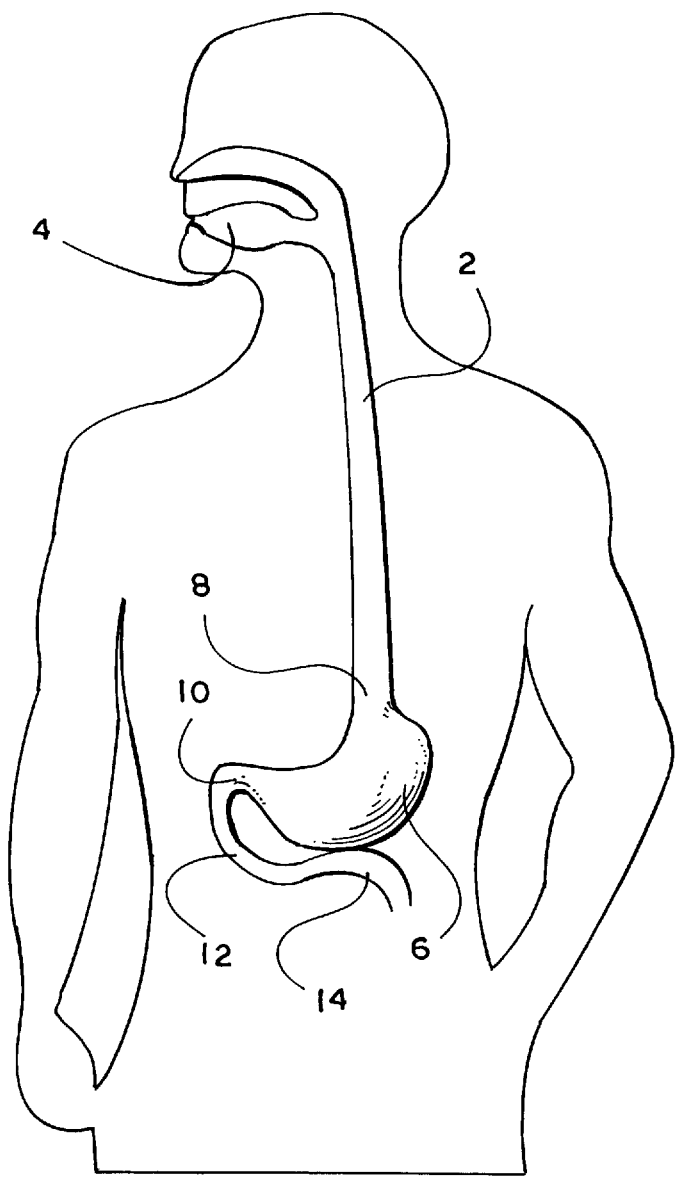
Fig_1

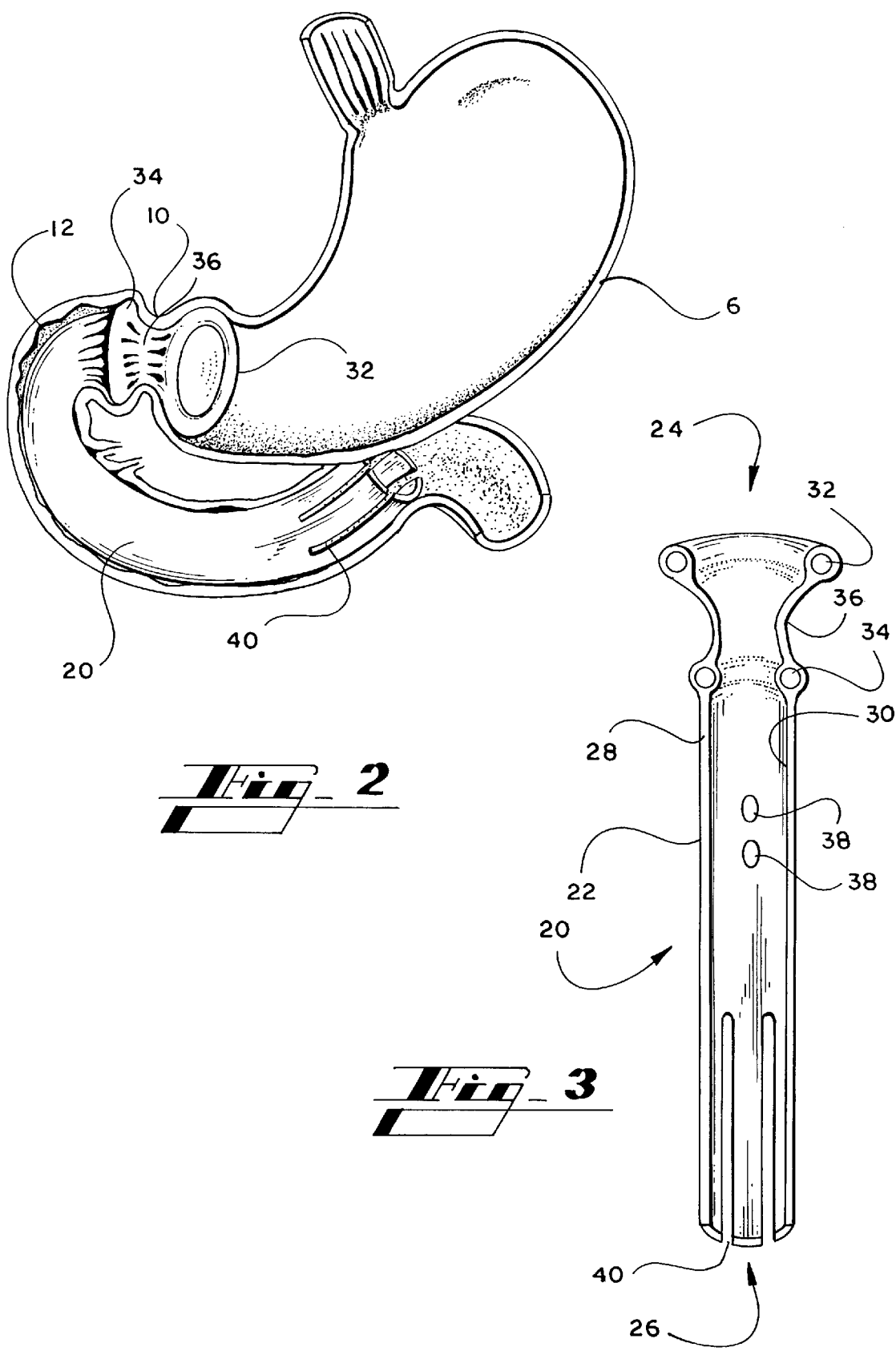

DUODENAL INSERT AND METHOD OF USE

BACKGROUND OF THE INVENTION

I. Field of the Invention

The present invention relates generally to the field of medical appliances. More particularly, the present invention relates to a device for lining a portion of the alimentary canal to control contact time of bile and digestive enzymes with food ingested by a human or other animals.

II. Description of the Related Art

It is well know that digestion starts with the chewing of and introduction of saliva with food in the mouth. Digestion continues in the stomach with the introduction of acid and some enzymes. After a residence period within the stomach, the partially digested food materials move into the duodenum for the further introduction of digestive fluids from the pancreas, liver and other organs. The action of these digestive fluids causes the further break down of the partially digested food materials into an absorbable form by the ileum and/or villi of the small intestine. By interrupting the intermixing of the digestive fluids and/or limiting the residence period within the stomach, the partially digested food materials will not fully digest into particles small enough to be absorbed by the body.

Smit in U.S. Pat. No. 4,315,509 describes insertion and removal catheters and intestinal tubes for restricting absorption. Particularly shown is a self-compressing, open-ended, balloon-like tube for implantation in and lining of the digestive tract. This device has a ring to keep one end of the tube open and a series of magnets to artificially simulate natural peristalsis. Anchoring of this device is accomplished by the single ring. However, unless the ring is surgically mounted, such as by sutures, staples or the like, to the wall of the stomach or any other organ within the alimentary canal, this device can move within the alimentary canal and close itself off from receiving consumed food materials.

SUMMARY OF THE INVENTION

In accordance with the present invention and the contemplated problems which have and continue to exist in this field, one of the objectives of this invention is to provide a duodenal insert that assists a patient in reducing his or her weight.

Many people cannot resist the temptation to eat, often causing them to engage in a starvation routine or resort to purging. It is therefore another objective of the present invention to provide a duodenal insert that enables one to consume what is a typical amount of food for them so that their urge to eat is satisfied with continued weight control.

Yet, it is another objective of the present invention enable a practitioner to control the amount of calories available for absorption by the body.

Still, it is another objective of the present invention to control intermixing of digestive fluids discharged by the body into the duodenum with partially digested food materials discharged from the stomach.

Even yet, it is another objective of the present invention to control the amount of time that ingested food remains in the stomach.

This invention accomplishes the above and other objectives and overcomes the disadvantages of the prior art by providing a duodenal insert that is simple in design and construction, inexpensive to fabricate, and easy to use. The duodenal insert consists of an open-ended tube having a pair of spaced apart rings disposed at one of the ends of the tube. The level of intermixing of digestive fluids with partially digested food materials is controlled by one or more bores optionally disposed through the wall of the tube. Additionally, slits are optionally provided at the opposite end of the tube from the rings to permit additional intermixing. The duodenal insert can be inserted via the mouth through the esophagus and the stomach, and positioned within the duodenum. To anchor the duodenal insert, the rings are manipulated such that the rings are separately disposed on each side of the pyloric opening. The duodenal insert may be removed from the body by retracting the device in reverse order through the stomach, esophagus and mouth. In some instances, a practitioner can implant the duodenal insert surgically, which enables the duodenal insert to be manufactured from a more rigid material.

It is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

Other objects, advantages and capabilities of the invention will become apparent from the following description taken in conjunction with the accompanying drawings showing preferred embodiments of the invention.

BRIEF DESCRIPTION OF THE DRAWINGS

The invention will be better understood and the above objects as well as objects other than those set forth above will become apparent when consideration is given to the following detailed description thereof. Such description makes reference to the annexed drawings wherein:

FIG. 1 is a schematic view of a portion of the gastrointestinal system of a human;

FIG. 2 is a sectional view of the stomach and duodenum with a duodenal insert made in accordance with the present invention secured in the pylorus and extending into the duodenum; and FIG. 3 is a sectional view of the duodenal insert of FIG. 2.

The reference numbers in the drawings relate to the following:

2=esophagus
4=mouth
6=stomach
8=esophageal-gastric juncture
10=pylorus
12=duodenum
14=jejunum
20=duodenal insert
22=open-ended tube
24=first end of open-ended tube
26=second end of open-ended tube
28=tube wall of open-ended tube
30=surface
32=first ring
34=second ring
36=pyloric conduit
38=bore
40=split

DESCRIPTION OF THE PREFERRED EMBODIMENTS

For a fuller understanding of the nature and desired objects of this invention, reference should be made to the following detailed description taken in connection with the accompanying drawings. Referring to the drawings wherein like reference numerals designate corresponding parts throughout the several figures, reference is made first to FIG. 1. FIG. 1 of the drawings illustrates an upper digestive tract of a human. The esophagus 2 terminates at the nose or mouth 4 at its superior end and at the stomach 6 at its inferior end. The wall of the stomach 6 encloses a chamber which is characterized, in part, by the esophageal-gastric juncture 8, which is an opening to the esophagus 2, and the pylorus 10, which is an opening to the duodenum 12. The stomach 6 empties through the pylorus 10 into the duodenum 12. Specifically, the pylorus 10 controls discharge from the stomach 6 by a sphincter muscle, the pyloric sphincter, which enables the pylorus 10 to open wide enough to pass about an object which is approximately one cubic centimeter or less. Gastric contents, after passing into the duodenum 12, continue on into the jejunum 14 and on into the ileum.

The duodenum 12 or first nine to ten inches of the small intestine is the only portion of the small intestine which is attached to the body. The remainder of the small intestine is not attached to the body, but merely folds freely in a sack called the mesentery, which is contained within the peritoneum.

Digestion starts with the chewing of food materials in combination with the action of saliva and enzymes secreted in the mouth 4. Within the stomach 6, digestion continues with the action of acids and additional enzymes secreted therein to produce partially digested food materials. After a short residence time in the stomach 6, the partially digested food moves further along the alimentary canal into the duodenum 12 to be intermixed with other digestive fluids which further digest the partially digested food materials to make the nutrients contained therein available for absorption by the villi and microvilli of the small intestine or by other absorptive organs of the body.

By interrupting or reducing the intermixing of the digestive fluids made available in the duodenum 12, the partially digested food materials are not readily absorbable by the small intestine or other absorptive organs of the body. The partially digested food materials are then passed to the large intestine for elimination from the body with limited caloric absorption by the body. The same effect can occur if the partially digested food materials are moved too quickly from the stomach 6 to the jejunum 14 or the ileum. It takes a certain amount of time for the digestive fluids introduced within the duodenum 12 to break down the partially digested food materials into an absorbable form having a small particle size. Even some liquid food materials have particle sizes that are too large to be absorbed without sufficient intermixing of the digestive fluids introduced within the duodenum 12 or without sufficient time for the digestive fluids to act.

Referring now to FIGS. 2 and 3, these Figures of the drawings illustrate a duodenal insert 20 made in accordance with the present invention. The duodenal insert 20 enables a practitioner to predeterminatively limit caloric absorption by the body by controlling the amount of digestive fluids introduced within the duodenum 12 which can intermix with the partially digested food materials and/or limiting amount of time for these digestive fluids to break down the partially digested food materials into an absorbable form. By limiting the body's ability to break down the partially digested food materials into an absorbable form, the practitioner can effectuate weight loss in a patient in a controlled manner. For example, if a patient has a history of being twenty percent (20%) overweight, it is readily apparent that the patient is consuming and/or absorbing too many calories from food. Accordingly, the practitioner can fit the patient with a duodenal insert 20 which allows only about eighty percent (80%) of the available calories from the food to be absorbable by the body.

As particularly shown in FIG. 2, the duodenal insert 20 is disposed within the duodenum 12 and anchored within the pylorus 10. With continued reference to FIGS. 2 and 3, the duodenal insert 20 comprises an elongated open-ended tube 22 having, a first end 24, a second end 26 and a tube wall 28 extending between the first an second ends 24 and 26. Within the open-ended tube 22 is a passageway that extends from the first end 24 to the second end 26 for transporting the partially digested food materials from the stomach 6 a predetermined distance below the stomach 6. Preferably, the passageway has a smooth and unobstructed surface 30 to enable the partially digested food materials to be squeezed through the open-ended tube 22 by natural peristalsis action of the alimentary canal. The duodenal insert 20 is preferably flexible to enable it to conform to the curves and contractions of the stomach 6, the duodenum 10 and other organs of the alimentary canal.

As previously mentioned, the duodenal insert 20 is anchored, preferably removably anchored, within the pylorus 10. The duodenal insert 20 may be implanted orally or surgically. If the duodenal insert 20 is implanted surgically, the duodenal insert 20 to be manufactured from a more rigid material. Since the duodenum 12 is attached to the body, the duodenal insert 20 can be manufactured of a relatively flexible material. At the first end 24 of the open-ended tube 22, is a first ring 32 which is attached around its circumference to the first end 24. The first ring 32 holds the first end 24 of the open-ended tube 22 open to receive the partially digested food materials from the stomach 6. It is preferred for the first ring 32 to be made of a collapsible, yet resilient material. Spaced a predetermined distance from the first ring 32 is a second ring 34. The second ring 34 is attached around its circumference to the open-ended tube 22 and holds the open-ended tube 22 open at that point to receive the partially digested food materials received by the first ring 32. It is likewise preferred for the second ring 34 to be made of a collapsible, yet resilient material. The open-ended tube 22 has a flexible pyloric conduit 36 extending from the first ring 32 to the second ring 34. In operation, the duodenal insert 20 is anchored by collapsing the second ring 34 and directing it through the pylorus 10. Once through the pylorus 10, the second ring 34 is permitted to return to its annular shape and seat adjacent the pylorus 10 within the duodenum 12. Preferably, the distance between the first and second rings 32 and 34, or in other words, the length of the pyloric conduit 36, is sufficient to permit the pyloric conduit 36 to extend through the pylorus 10 and allow the first and second rings 32 and 34 to encircle and to seat adjacent the pylorus 10 within the stomach 6 and within the duodenum 12, respectively. In this manner, the pylorus 10 is sandwiched between the first and second rings 32 and 34, and the pyloric sphincter engages the pyloric conduit 36 to anchor the duodenal insert 20 within the pylorus 10. Clearly, the first and second rings 32 and 34 should be larger than the opening of the pylorus 10. Additionally, the second ring 34 must be able to pass through the pylorus 10 while in a collapsed state without damaging the tissue of the pylorus 10. Depending either upon the length or the flexibility of the material of the pyloric conduit 36, or a combination of both, the pylorus 10 can be kept open to varying degrees or be permitted to naturally close. By controlling the opening of the pylorus 10, the practitioner can control the time food materials are permitted to remain within the stomach 6, thereby predetermitively limiting the level of break down of partially digested food materials for absorption. To implant the duodenal insert 20 orally, the duodenal insert 20 is collapsed, preferably along a longitudinal axis of the duodenal insert 20 extending from the first end 24 to the second end 26, and inserted through the mouth 4, the esophagus 2 and the stomach 6, anchored within the pylorus 10 and extended into the duodenum 12.

By anchoring the duodenal insert 20 within the pylorus 10, the digestive fluids made available by the body in the duodenum 12 for intermixing with the partially digested food materials exiting the stomach 6 can be interrupted or reduced. Essentially no or very little intermixing occurs within the duodenal insert 20 when the tube wall 28 is fabricated with a nonpermeable material. With continuing reference to FIG. 3, bores 38 are shown disposed through the tube wall 28 to provide the digestive fluids controlled access to the interior of the duodenal insert 20. This feature provides the practitioner with the ability to control the intermixing of digestive fluids discharged by the body into the duodenum 12 with the partially digested food materials contained within the duodenal insert 20. The amount of digestive fluids entering the duodenal insert 20 is controlled by the size and number of the bores 38 and the location of the bores 38 with respect to the ducts delivering the digestive fluids to the duodenum 12.

Also shown in FIGS. 2 and 3 are splits 40 disposed along the tube wall 28, which provide controlled access to the interior of the duodenal insert 20. As with the bores 38, the splits 40 provide the practitioner with the ability to control the intermixing of digestive fluids discharged by the body into the duodenum 12 with the partially digested food materials contained within the duodenal insert 20. The amount of digestive fluids entering the duodenal insert 20 is controlled by the length, width and number of the splits 40 and, likewise, the location of the splits 40 with respect to the ducts delivering the digestive fluids to the duodenum 12. The splits 40 may be located anywhere along the tube wall 28. With the embodiments shown in FIGS. 2 and 3, the splits 40 extend from the second end 26 for a predetermined distance toward the first end 24.

The materials of construction of the duodenal insert 20 are not highly critical so long as they are compatible with the body tissues and fluids involved. Such useful materials are, for example, dacron, latex and silicone, but these materials are illustrative only and are non-exclusive. In an alternate embodiment of the present invention, the duodenal insert 20 can be fabricated from materials which biodegrade in the alimentary canal after preselected periods of time. In this manner, the practitioner can select the appropriate biodegradation time so that the duodenal insert 20 can be removed from the alimentary canal by normal processes at such time as it has achieved the desired physiological result. Yet, in another embodiment of the present invention, the tube wall 28 can be manufactured from a porous material which provides controlled intermixing of digestive fluids discharged by the body into the duodenum 12 with the partially digested food materials contained within the duodenal insert 20. As with the bores 38, amount of digestive fluids entering the duodenal insert 20 is controlled by the size and number of the pores (not shown).

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. A duodenal insert for placing within an alimentary canal of an animal and controlling intermixing of digestive fluids with partially digested food materials exiting a stomach, the duodenal insert comprising:

a flexible, elongated open-ended tube having a first end and a second end, the open-ended tube having a passageway extending from the first end to the second end for transporting the partially digested food materials within a smooth and unobstructed surface to enable the partially digested food materials to be squeezed through the tube by natural peristalsis action of the alimentary canal; and a pylorus anchoring means at the first end engagable with a pyloric sphincter for anchoring the open-ended tube within a pylorus of the animal.

2. A duodenal insert as claimed in claim 1, wherein the pylorus anchoring means comprises:

a resilient first ring attached around its circumference to the first end of the open-ended tube for holding open the open-ended tube to receive the partially digested food materials from the stomach, the first ring placeable within the stomach adjacent the pylorus, a resilient second ring attached around its circumference to the open-ended tube a predetermined distance from the first end for holding open the open-ended tube to receive the partially digested food materials from the first ring, the second ring placeable within a duodenum adjacent the pylorus; and a flexible pyloric conduit extending from the first ring to the second ring, placeable through the pylorus and engagable with the pyloric sphincter, whereby the first and second rings sandwich the pylorus and the pyloric sphincter engages the pyloric conduit to anchor the duodenal insert.

3. A duodenal insert as claimed in claim 2, wherein the pyloric conduit is made of a resilient material, whereby the pylorus remains open.

4. A duodenal insert as claimed in claim 1, wherein the open-ended tube has a tube wall and at least one bore disposed through the tube wall.

5. A duodenal insert as claimed in claim 1, wherein the open-ended tube has a tube wall and a plurality of bores disposed through the tube wall.

6. A duodenal insert as claimed in claim 1, wherein the open-ended tube has a tube wall and the tube wall has at least one split.

7. A duodenal insert as claimed in claim 1, wherein the at least one split extends from the second end for a predetermined distance toward the first end.

8. A duodenal insert as claimed in claim 1, wherein the open-ended tube has a tube wall and the tube wall has a plurality of splits.

9. A duodenal insert as claimed in claim 1, wherein the plurality of splits extend from the second end for respective predetermined distances toward the first end.

10. A method for effecting weight loss by a patient, comprising:

provid ing, a duodenal insert having a flexible, elongated open-ended tube having a first end, a second end and a longitudinal axis between the first and second ends, the open-ended tube having a passageway extending from the first end to the second end for transporting partially digested food materials within a smooth and unobstructed surface to enable the partially digested food materials to be squeezed through the tube by natural peristalsis action of the alimentary canal, and a pylorus anchoring means at the first end engagable with a pyloric sphincter for anchoring the open-ended tube within a pylorus;

collapsing the duodenal insert along a longitudinal axis of the insert;

per-orally inserting the collapsed duodenal insert into the stomach through the esophageal-gastric juncture;

inserting the pylorus anchoring means into the pylorus;

releasing the collapsing force to cause the collapsed duodenal insert to autogenously reassume and retain its normal shape;

manipulating the second end of the duodenal insert into the duodenum; and maintaining the duodenal insert within the pylorus and the duodenum for a length of time sufficient to cause a weight loss by the patient.

11. A method as claimed in claim 10, wherein the duodenal insert is implanted surgically.

* * * * *